United States Patent [19]
Kageyama et al.

[11] Patent Number: 4,984,567
[45] Date of Patent: Jan. 15, 1991

[54] APPARATUS FOR MEASURING INTRACRANIAL PRESSURE

[75] Inventors: Naoki Kageyama, Kyoto; Hiroji Kuchiwaki, Aichi; Junki Ito, 1-12, Harayamadai, Seto-shi, Aichi 489; Nobumitsu Sakuma; Yukio Ogura, both of Ibaraki, all of Japan

[73] Assignees: Hitachi Construction Machinery Co., Ltd., Tokyo; Hiroji Kuchiwaki, Aichi, both of Japan

[21] Appl. No.: 350,705

[22] PCT Filed: Sep. 25, 1987

[86] PCT No.: PCT/JP87/00705
§ 371 Date: Apr. 17, 1989
§ 102(e) Date: Apr. 17, 1989

[87] PCT Pub. No.: WO88/02234
PCT Pub. Date: Apr. 7, 1988

[30] Foreign Application Priority Data
Sep. 27, 1986 [JP] Japan ................................ 61-227139

[51] Int. Cl.$^5$ .............................................. A61B 8/00
[52] U.S. Cl. .......................... 128/660.02; 128/661.05
[58] Field of Search ...................... 128/660.01, 660.02, 128/661.05, 660.06; 73/599, 602

[56] References Cited

U.S. PATENT DOCUMENTS

| | | | |
|---|---|---|---|
| 3,853,117 | 12/1974 | Murr | 128/660.02 |
| 4,453,550 | 6/1984 | Flax | 128/660.01 |
| 4,483,345 | 11/1984 | Miwa | 128/660.02 |
| 4,593,703 | 6/1986 | Cosman | 128/660.02 X |
| 4,648,276 | 3/1987 | Klepper et al. | 73/602 X |
| 4,655,228 | 4/1987 | Shimura et al. | 73/602 X |
| 4,723,553 | 2/1988 | Miwa et al. | 128/660.06 |

FOREIGN PATENT DOCUMENTS
60-148545 8/1985 Japan .

Primary Examiner—Francis Jaworski
Attorney, Agent, or Firm—Wenderoth, Lind & Ponack

[57] ABSTRACT

The present invention relates to an apparatus for measuring the intracranial pressure of a living body or patient utilizing ultrasonic waves. An ultrasonic pulse is transmitted as triggered by a trigger signal into the cranium from an ultrasonic probe placed outside the cranium of the living body, the data of an interference reflection wave caused by the multiple reflections of the incident waves at the interstital boundaries within the cranium is analyzed for frequency, and the time difference between the element waves of the interference reflection wave is calculated and delivered as output. Thus, the dura mater thickness and its change are measured, and the intracranial pressure and its change can be measured utilizing the correlation between the intracranial pressure and dura mater thickness.

The most of the conventional measurements of intracranial pressure are done with an invasion to the cranium, and some noninvasive techniques have been proposed but their accuracy and costs are far from the level at which they can be satisfactorily used. The apparatus according to the present invention permits to measure the intracranial pressure from outside the cranium, easily, safely, highly reliably, non-invasively and without any malinfluence on the brain inside. Furthermore, by periodically effecting such measurement, the intracranial pressure and the pattern of its change can be known and accurate diagnostic information on the pathology as well as legion-preventive information can be provided.

2 Claims, 17 Drawing Sheets

APPARATUS FOR MEASURING INTRACRANIAL PRESSURE

FIELD OF THE INVENTION

The present invention relates to an apparatus for measuring the intracranial pressure using the ultrasound technique (will be referred to as "cephalohemometer" hereinafter) and more particularly to an ultrasonic cephalohemometer suitably usable for measuring the intracranial pressure noninvasively and safely from outside the cranium.

BACKGROUND ART

The human being in the normal condition, that is, in good health, has a constant intracranial cavity volume peculiar to himself. However, if he suffers from, for example, a lesion such as cerebral tumor, hematoma or the like or any other intracranial disease, the volume of the intracranial cavity is increased. It is said that when the increase reaches about 10% of the normal cavity volume, the intracranial pressure rises and leads to a sthenia of the intracranial pressure, whereby a variety of diseases will be caused. To make clear what these diseases and determine appropriate therapy for them, it is necessary to throw a pathologic light on the sthenia of intracranial pressure. The means and methods for such elucidation have been studied in various fields of medicine, but no satisfactory means and methods have yet been proposed. However, one of the most important means for the elucidation is the measurement of the intracranial pressure Heretofore, various many methods of measuring the intracranial pressure have been studied and tried. Such conventional methods include, for example, the latex baloon method in which a latex baloon charged with water is introduced above the dura mater or into the cerebral ventricle inside the cranium to measure the water pressure in the baloon, thereby measuring the intracranial pressure and the EDP measuring method in which a part of the cranium is opened to make an osseous window through which the dura mater is exposed, a strain gauge is put into contact with the dura mater and a change of the intracranial pressure is measured as a change of strain measured by a dynamic strain gauge connected to the strain gauge. However, since the measurement of the intracranial pressure by these methods is done with an invasion to the cranium, the patient must be subject to a craniotomy and have a sensor placed inside the cranium. Thus, the conventional methods for intracranial pressure measurement have problems since the patient must bear a heavy physical and socioeconomic burdens because he has the possibility of being infected and must be in rest as hospitalized to maintain his health. In addition to the above-mentioned methods, there has been proposed a telemetry system, as a noninvasive and safe method, in which an electric resonant circuit composed of an inductance and capacitance is used of which the resonant frequency is changed by changing one of the values, inductance or capacitance, with the dislocation of a bellows or diaphragm due to the intracranial pressure and measured from above the scalp. However, this method also have practical problems; since air is used as compression medium, it, if any between the scalp and cranium , is easily affected by the temperature, the measuring gradation is required for each patient and the measuring accuracy is also far from the practical use. Heretofore, there has not yet been provided any cephalohemometer which can measure the intracranial pressure easily, noninvasively without any malinfluence on the brain inside and with a high reliability, and those in the clinical fields have long waited for such cephalohemometer.

As having been described in the foregoing, the cephalohemometry has been done by the methods with an invasion to the cranium in almost all the cases while being one of the most important means in the elucidation and therapy of the intracranial pressure sthenia. There have not yet been proposed any method and apparatus which satisfy the required safety and reliability for the measurement and can make the measurement with a reduced socioeconomic burden to the patient. On the other hand, the cephalohemometry by the noninvasive method is just under study and development, and the accuracy and costs thereof are not yet at the practical stage.

The present invention has an object to overcome the above-mentioned drawbacks of the conventional techniques by providing an ultrasonic cephalohemometer which can measure the intracranial pressure from outside the cranium easily, safely, noninvasively, highly reliably and without any malinfluence on the brain inside.

DISCLOSURE OF THE INVENTION

According to an aspect of the present invention, an ultrasonic cephalohemometer is provided which has an electrocardiograph which detects the heart beat of a living body or patient, a pulser which generates a voltage pulse taking as trigger the heart beat detected by the electrocardiograph, an ultrasonic probe which receives the pulse generated from the pulser, transmits an ultrasonic pulse into the cranium of the patient from the outside thereof and receives the echo of the incident wave, a receiver which amplifies the received echo, and a processor which processes the output from the receiver, comprising:

an A/D converter which digitizes the discrete values of the echo waveform received by the probe; and an arithmetic unit which extracts from the output from the A/D converter a range including the reflection wave from the dura mater, determines a time difference between element waves from a quefrency value obtained through frequency analysis of the extracted range by the arithmetic algorithm of cepstrum method, thereby calculating the thickness of the dura mater, and compares the calculated dura mater thickness with a previously measured reference value for thereby calculating a dura mater distortion factor in a correlation with the intracranial pressure.

According to another aspect of the present invention, an ultrasonic cephalohemometer is provided which has an electrocardiograph which detects the heart beat of a living body or patient, a pulser which generates a voltage pulse taking as trigger the heart beat detected by the electrocardiograph, an ultrasonic probe which receives the pulse generated from the pulser, transmits an ultrasonic pulse into the cranium of the patient from the outside thereof and receives the echo of the incident wave, a receiver which amplifies the received echo, and a processor which processes the output from the receiver, comprising:

a gate circuit which gates the echo received by the probe to a range including the reflection waves from the dura mater to deliver a waveform within the gate;

an A/D converter which digitizes the discrete values of the output waveform from the gate circuit; and an arithmetic unit which determines a time difference between element waves from a quefrency value obtained through frequency analysis of the output from the A/D converter by the arithmetic algorithm of cepstrum method, thereby calculating the thickness of the dura mater, and compares the calculated dura mater thickness with a previously measured reference value for thereby calculating a dura mater distortion factor in a correlation with the intracranial pressure.

The above-mentioned first and second ultrasonic cephalohemometers utilize the correlation between the intracranial pressure and dura mater thickness, verified by the Inventor et al, based on which the intracranial and its change can be measured by measuring the dura mater thickness and its change (thickness strain).

The thickness of the dura mater and its change are measured in both the first and second ultrasonic cephalohemometers by utilizing the output derived from the calculation of the difference in propagation time between the element waves of the interference wave as mentioned above. The output of the difference in propagation time between the element waves is first connected to the pulse taking an arbitrary trigger pulse as trigger signal, and a transmission pulse is sent from the pulser to the probe disposed outside the patient's cranium and which is connected to the pulser. In the probe, the transmission pulse sent from the pulser is converted to an ultrasonic pulse which is transmitted into the cranium. Then the ultrasonic wave transmitted into the cranium is reflected at various interstital boundaries being the acoustic boundaries such as skull, dura mater, etc., and the reflection waves interfere with each other while being subject to the transmission loss and reflection loss. The echo of the interference reflection wave is received by the probe. The reflection wave from each interstital boundary, which forms the interference waveform of this received echo, that is, a wave having a same waveform as the incident wave and of which the amplitude decreases along the path, will be described as the element wave herein In the first cephalohemometer, the echo received by the probe is sent to the receiver in which it is amplified, and this amplified echo is sent to the A/D converter where the discrete values of the received waveform are converted from analog to digital The output from the A/D converter is sent to the arithmetic unit. In the arithmetic unit, digital data including the waveform discrete values of the above-mentioned interference reflection waveform resulted from the reflections within the cranium is extracted and this extracted data is analyzed for frequency to provide a difference in propagation time between the element waves of the interference wave.

In the second cephalohemometer, the echo received by the probe is sent to the receiver where it is amplified, and the amplified signal is sent to the gate circuit. On the other hand, the gate circuit is supplied with the above-mentioned trigger pulse which is used as trigger signal to provide an arbitrary delay time from the rise of the pulse and gate, by an arbitrary time duration, the received echo sent through the receiver so as to include the interference reflection wave, thereby delivering an gated-in waveform. This output waveform is sent to the A/D converter in which it is converted from analog to digital and the output from the A/D converter is sent to the arithmetic unit. In this arithmetic unit, a means such as frequency analyzer in provided to generate a difference in propagation time between the element waves of the interference reflection wave.

As having been described in the foregoing, since both the first and second cephalohemometers are so designed as to calculate and deliver a difference in propagation time between the elements waves, it is possible to measure the dura mater thickness and its change and also to measure the intracranial pressure and its change easily, safely and noninvasively, based on the correlation between the intracranial pressure and dura mater thickness which will be further described later with reference to the embodiments of the present invention.

Also, by connecting a display unit such as CRT monitor or a recorder like a printer, floppy disk unit or the like to the above-mentioned arithmetic unit, it is possible to display or record the above-mentioned measured values which will thus be utilized more conveniently as diagnostic and clinical information.

BRIEF DESCRIPTION OF THE DRAWINGS

All the drawings attached are to explain the present invention, of which,

FIGS. 1 and 2 relate to a first embodiment of the present invention, FIG. 1 showing the system configuration of the first embodiment of the cephalohemometer according to the present invention while FIG. 2 is an operation-explanatory drawing showing the output pulses at various functional steps;

FIGS. 3 and 4 relate to a second embodiment of the present invention, FIG. 3 being the system configuration of the second embodiment of the cephalohemometer according to the present invention while FIG. 4 is an operation-explanatory drawing showing the output pulses at various functional steps;

BEST MODE FOR CARRYING OUT THE INVENTION

Figure 1:
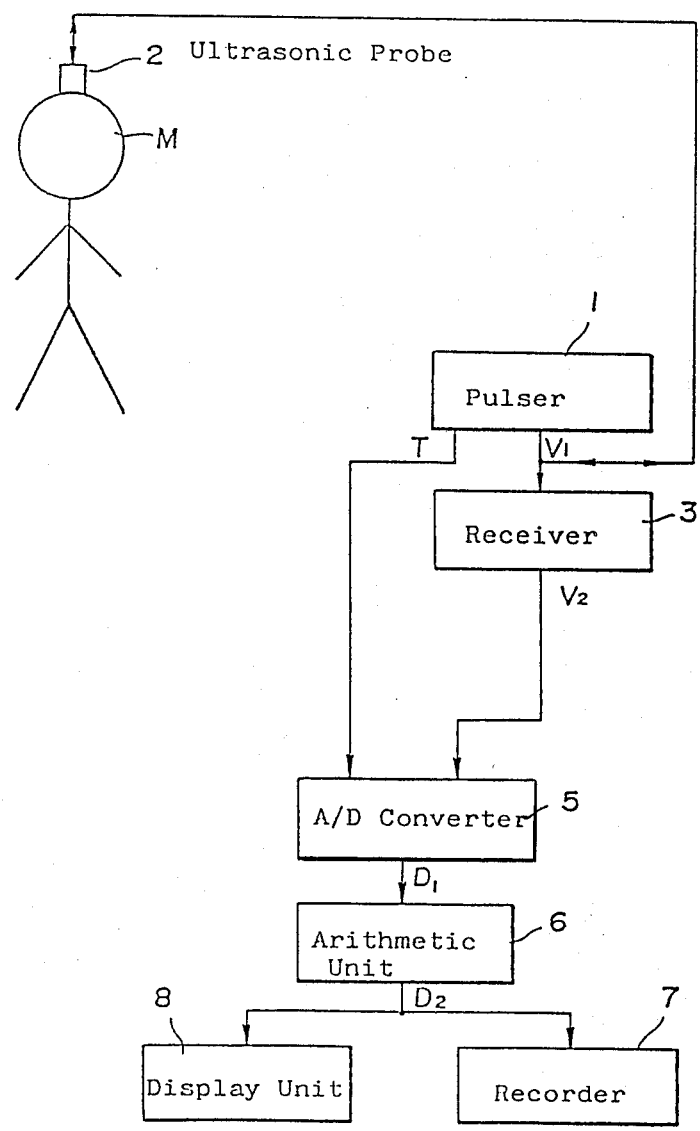
Figure 2:
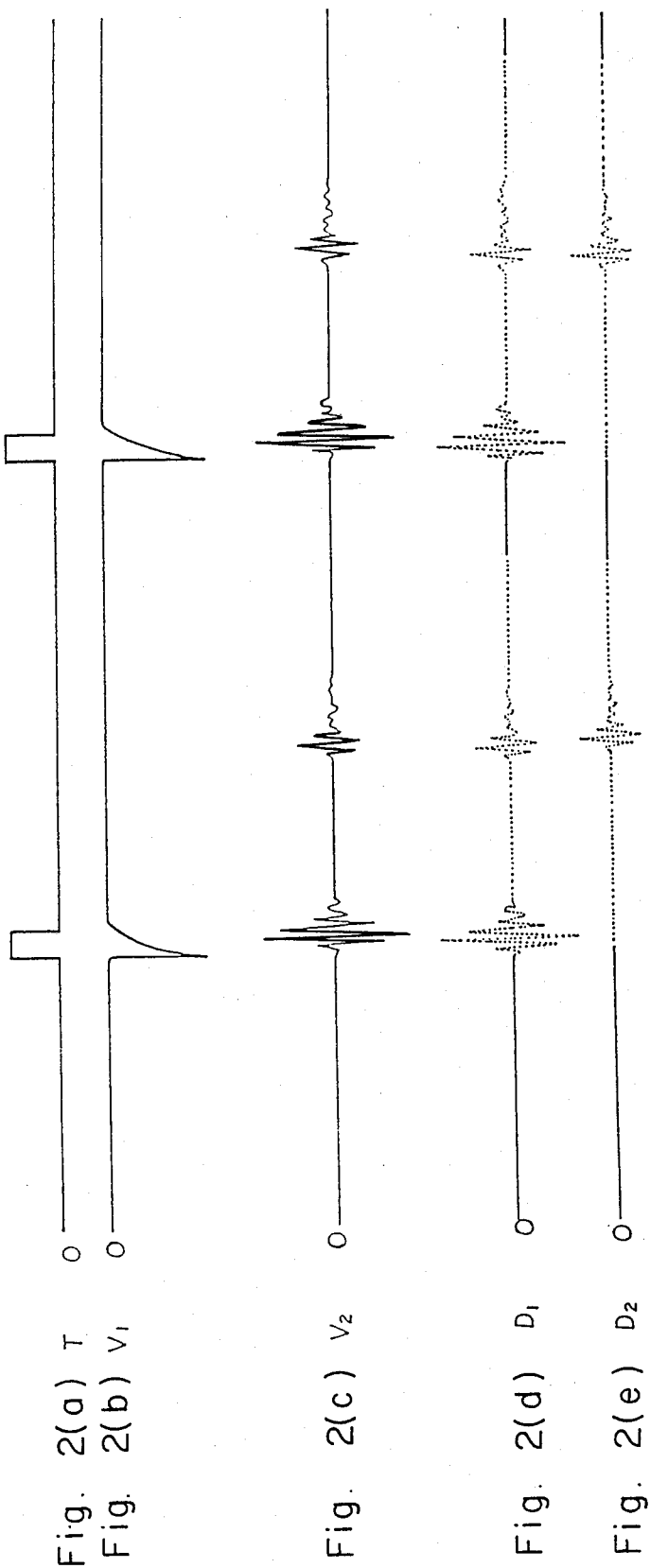

The first embodiment of the present invention will be explained with reference to FIGS. 1 and 2. FIG. 1 shows the system configuration of the cephalohemometer and FIG. 2 is an operation-explanatory drawing showing the output pulses at various functional step. In Figures, the reference numeral 1 indicates a pulser connected to a probe 2 placed on the skull of the patient M and which transmits a transmission pulse V1 shown in FIG. 2 (b) to the probe 2 simultaneously with the rise of the internal trigger pulse T shown in FIG. 2 (a).

The probe 2 converts the transmission pulse V1 to an ultrasonic pulse which will be transmitted into the cranium.

The ultrasonic pulse transmitted into the cranium is subject to the reflections at various interstital boundaries being the acoustic boundaries such as skull, dura mater, etc., and the reflection waves interfere with each other while being subject to the transmission loss and reflection loss. The reflection waves include the reflection waves from the inner and outer surfaces of the dura mater and the multiple-reflection waves from the dura mater. The echo of the interference reflection wave from these reflection waves is also received by the probe 2. The reference numeral 3 indicates a receiver which amplifies the echo including the interference reflection wave received by the probe 2 and delivers an echo V2 shown in FIG. 2 (c).

The reference numeral 5 indicates an A/D converter which receives an amplified echo including the interference wave delivered from the receiver 3, converts it from analog to digital taking the pulse T as trigger signal and delivers a digital waveform signal D1 consisting of the discrete values of the echo waveform shown in FIG. 2 (d). This digital waveform signal D1 is sent to an arithmetic unit 6 which extracts data in a range including the digital waveform of the interference wave and analyzes for frequency the data to calculate the time difference between element waves forming together the interference wave.

Figure 3:
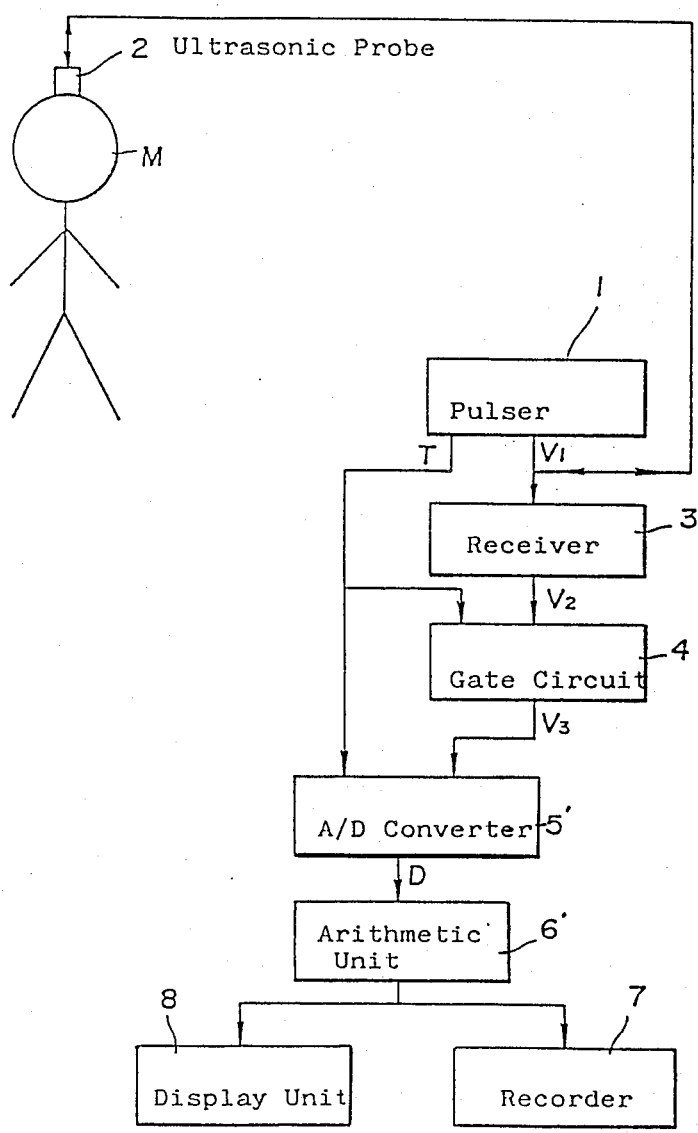
Figure 4:
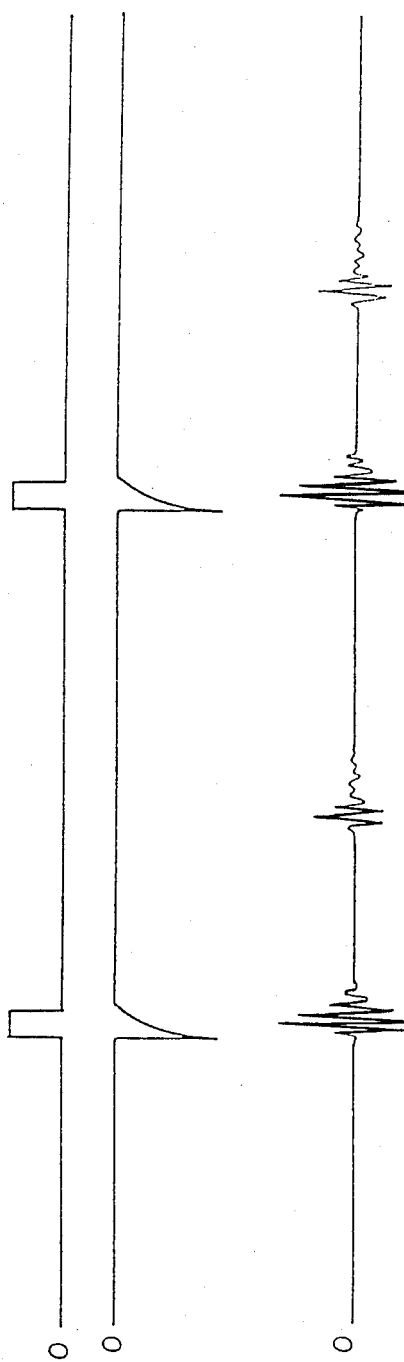

Next, a second embodiment of the cephalohemometer according to the present invention will be described with reference to FIGS. 3 and 4. FIG. 3 is the system configuration of the cephalohemometer and FIG. 4 is an operation-explanatory drawing showing the output pulses at various functional steps. In Figures, the same reference numerals as in FIGS. 1 and 2 indicate the same elements as in FIGS. 1 and 2. The explanation having been made of the first embodiment with reference to FIGS. 1 and 2 up to the delivery of the echo V2 shown in FIG. 2 (c) is also true for this second embodiment except that "FIG. 1" should be replaced with "FIG. 3" and "FIG. 2" with "FIG. 4". The reference numeral 4 indicate a gate circuit which is supplied with the echo V2 from the receiver 3 and the above-mentioned internal trigger pulse T to delay the echo V2 an arbitrary time from the rise of the pulse T as trigger signal and gate, by an arbitrary time duration, the echo V2 delivered from the receiver 3 so as to include the interference reflection wave, thereby delivering an gated-in waveform V3 as shown in FIG. 4 (d). The reference numeral 5' indicates an A/D converter which is supplied with the gated-in waveform V3 delivered from the above-mentioned gate circuit 4 and converts the gated-in waveform V3 from analog to digital taking the above-mentioned pulse T as trigger signal, thereby generating a digital waveform signal D shown in FIG. 2 (a). This digital waveform signal D is sent to an arithmetic unit 6' in which a time difference between elements waves forming together the above-mentioned interference reflection wave is calculated by a frequency analysis.

The algorithm used in the aforementioned first and second embodiments uses the cepstrum method which will be described later, and the time difference between the element waves is obtained from the quefrency value calculated by the cepstrum method. The result of this calculation is sent to a display unit 8 on which it will be displayed and also to a recorder 7 in which it will be recorded. In the first embodiment having not the above-mentioned gate circuit, generally calculation data are fetched from the memory in CPU and displayed on the CRT for the above-mentioned extraction. So the calculation takes a correspondingly longer time but the waveform will have less strain since it is not passed through the gate circuit. On the contrary, in the second embodiment having the gate circuit, the output waveform sent through the gate circuit to the A/D converter where it is converted from analog to digital to provide an output value. This output value may be calculated as it is. Therefore, the memory may be of a correspondingly smaller capacity though this depends upon the magnitude of the gate width, and the operation is facilitated correspondingly.

In the above-mentioned first and second embodiments, an electrocardiograph trigger apparatus is used which provides, each time an R-wave of electrocardiogram (ECG) is generated as obtained by on an electrocardiograph connected to the patient M, a delay of an arbitrary time (for example, at every 80 to 100 msec) from the peak position of the R-wave to produce continuous pulses which can be used as the trigger signal.

To verify the correlation that as the intracranial pressure increases, the dura mater thickness changes correspondingly, on which the measurement by the above-mentioned apparatus is based, the Inventor effected the following experiments on a filial grown-up dog weighing about 10 kg. An osseous window was made in the left parietal region of the dog, and a colorless transparent PVC plate was fitted in the window. The change of the state of the veins in the dura mater due to the intracranial pressure was observed and photographed. The sthenia of intracranial pressure was caused by injecting a saline into the cisterna magna to raise the intracranial pressure from 0 mmH$_2$O (reference value before the rise of intracranial pressure) up to 700 mmH$_2$O. The observation and photography of the veins in the dura mater revealed that the veins in the dura mater appeared rather definite and showed no disturbance of the blood flow therein and that as the intracranial pressure rose, the veins in the dura mater were gradually constricted and fully constricted with no blood flow therein when the intracranial pressure reached about 600 mmH$_2$O. On the other hand, even when the intracranial pressure was lowered to less than 600 mmH$_2$O, the veins in the dura mater remained constricted. When the pressure fell down to around 200 mmH$_2$O, the blood flow was resumed in the veins. The occurrence of the constriction of the veins in the dura mater reveals that the dura matter was made thinner as compressed, and the dura matter became increasingly thinner as the intracranial pressure rose until it reached about 600 mmH$_2$O. Then the thickness of the dura mater showed no change even with the intracranial pressure further increased. Namely, it was proved that there is a correlation between the dura mater thickness and intracranial pressure.

Figure 5:
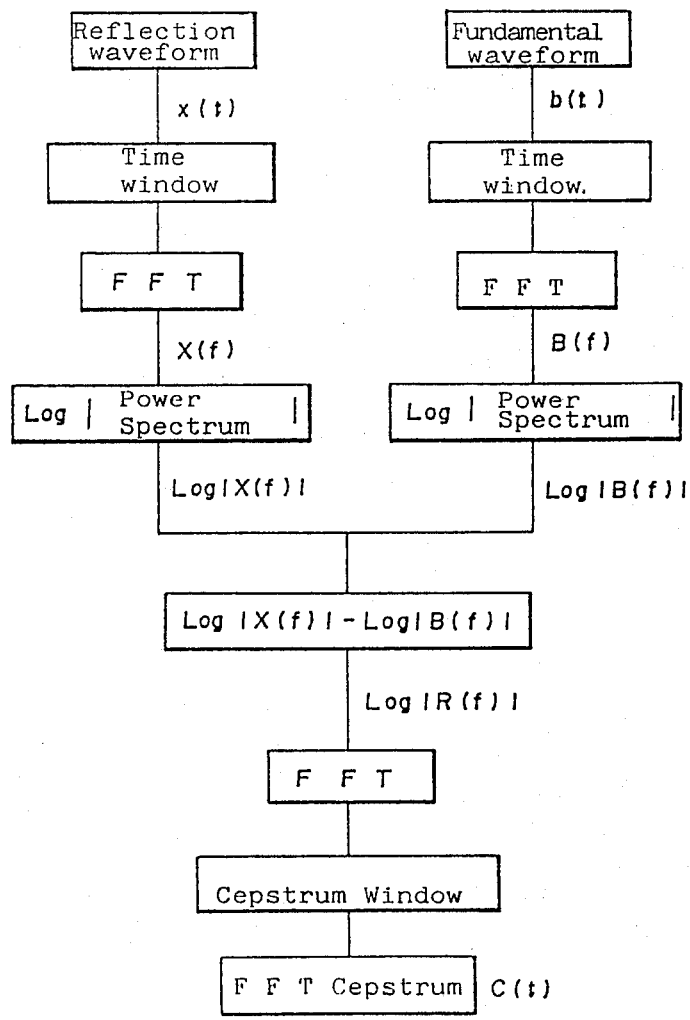
FIG. 5 is a drawing showing the algorithm for the cepstrum analysis.

The measurement according to the present invention is to know the intracranial pressure by measuring the thickness of the dura mater based on the aforementioned correlation between the strain of the dura mater thickness and the intracranial pressure. The measurement of the dura mater thickness is done by applying to the analysis of the thin-layer multiple-reflection wave the cepstrum analysis method worked out in the field of seismic wave analysis for the purpose of separating, by approximation, the direct wave and the waves traveling through the other paths from each other. The algorithm of the cepstrum analysis used in the embodiment of the present invention is shown in FIG. 5.

The cepstrum analysis method is such that the lengths of delay time of random waves derived from the superposition of delayed echoes are analyzed. A spectrum of the time series of the random waves is calculated, and a logarithm of this spectrum is also calculated. This logarithmic spectrum can be presented in the form of a diagram showing the logarithmic spectrum along the vertical axis and the frequency along the horizontal axis. Since the horizontal axis showing the frequency can be regarded as time base, the logarithmic spectrum can be presented as a frequency series. Since the logarithmic spectrum developed as this frequency series appears as a waving curve, the logarithmic spectrum can be subjected to the Fourier analysis to analyze what lengths of time delay the echo components of the frequency series have. This method is called the "cepstrum analysis". Namely, the frequency and spectrum when the time series is subjected to the Fourier transformation and which correspond to those when the frequency series is subjected to the Fourier transformation are called "Quefrency" and "Cepstrum", respectively. Therefore, when the frequency series is subjected to the Fourier transformation, a curve can be present which shows the cepstrum along the vertical axis while showing the quefrency along the horizontal axis. The value of this cepstrum corresponds to the magnitude of the echo and the value of the quefrency along the horizontal axis corresponds to the delay time of the echo.

The cepstrum analysis method is well known from, for example, "Spectrum Analysis" by Mikio Hino, Sept. 15, 1987, 15th printing, published by Asakura Shoten, pp. 280 to 283, and so it will not be explained in further detail.

Next, the application of the cepstrum analysis method to the intracranial echo will be explained below.

As seen in FIG. 5, the reflection wave from the boundary between the skull and dura mater is an interference wave resulted from the reflection wave (fundamental wave) from the boundary between the skull and dura mater and the multiple-reflection wave. Assume that the interference reflection wave from the boundary is x(t), fundamental wave is b(t), reflection intensity is ai and delay time is $\tau i$, and the interference reflection wave x(t) is expressed as follows:

$$x(t) = \sum_{i=0}^{n} a_i \cdot b(t + \tau_i) \tag{1}$$

the result of the Fourier transformation of both sides of the equation (1) is shown below:

$$x(f) = B(f) \sum_{i=0}^{n} a_i \cdot e^{j2\pi f \tau i} \tag{2}$$

where x(f) and B(f) are the results of Fourier transformation of x(t) and b(t), respectively. From the equation (2), the power spectrum $|X(f)|$ of X(f) is expressed as follows using the power spectrum $|B(f)|$ of B(f):

$$|X(f)| = |B(f)| \sum_{i=0}^{n} \sum_{k=0}^{n} a_i \cdot a_k \cos\{2\pi f(\tau_i + \tau_k)\} \tag{3}$$

The logarithm of the equation (3) is the following equation (4), and the interference reflection wave is separated into a frequency series being the power spectrum of the fundamental wave and a frequency series having a waving frequency on the frequency axis corresponding to the delay time difference.

$$\log|X(f)| = \log|B(f)| + \tag{4}$$
$$\left[ \sum_{i=0}^{n} \sum_{k=0}^{n} a_i \cdot a_k \cos\{2\pi f(\tau_i + \tau_k)\} \right]$$

Therefore, by determining a cepstrum through a further Fourier transformation of the equation (4), a quefrency series of the delay time on the quefrency axis can be determined, and so, if the acoustic velocity of a thin layer is known, the thickness of the layer can also be known.

In fact, the received wave resulted from an ultrasonic wave transmitted into the cranium is a complicate interference wave resulted from mutual interference between the reflected waves from the tissues such as skull, dura mater, etc. and the reflected waves derived from the multiple reflections within such tissues. Therefore, the aforementioned quefrency series represents the difference in time delay between the reflection waves from these intracranial tissues, and so it is necessary to discriminate the quefrency values corresponding to the reflection waves from inside and outside the dura mater from the above-mentioned reflection waves. The intracranial pressure varies as the heart beat changes, and as described in the above, the dura mater thickness changes as the intracranial pressure changes. On the other hand, since the skull will not be affected by the intracranial pressure, the above-mentioned measurement is repeated several times to discriminates the reflection waves from the dura mater from among those of which the quefrency values vary. Not only the dura mater changes in thickness as the intracranial pressure changes. However, since the dura mater exists just below the skull, the reflection waves of which the quefrency values do not vary just after the ultrasonic wave is transmitted into the cranium are the waves reflected at the skull, and the reflection wave next received and of which the quefrency value vary, that is, the first reflection wave of which the quefrency value vary, can be judged to be the reflection wave from the dura mater. After the reflection wave from the dura mater can be discriminated by the above method, it is necessary to measure the intracranial pressure in a certain phase during pulsation of the intracranial pressure which varies as the heart beat changes in order to eliminate the variation due to the heart beat. For this reason, the output of the electrocardiograph is used as trigger pulse to the pulser 1 as having been previously described.

Thus, this method can be used to measure the thickness of the dura mater.

Figure 6:
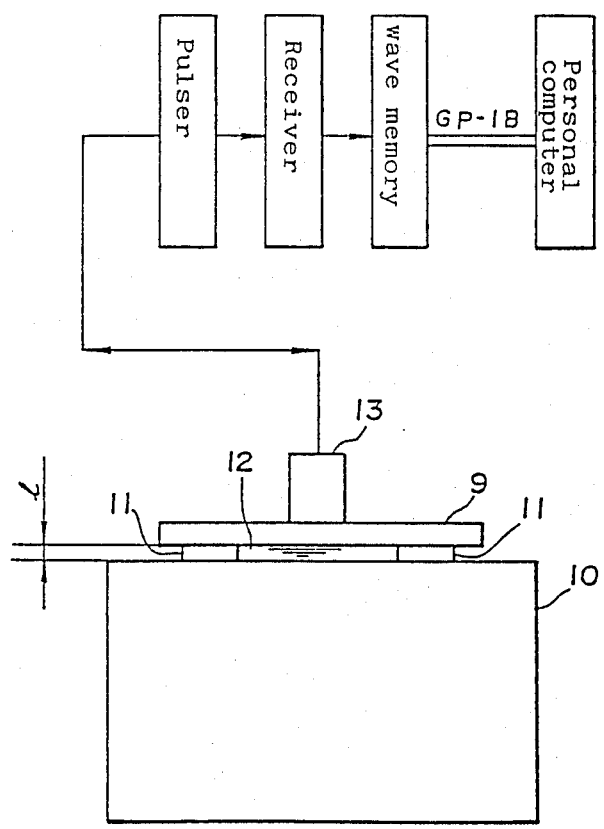
FIG. 6 is a drawing showing the experimental apparatus used for verification of the application of the cepstrum analysis.

Next, for verification of the aforementioned cepstrum analysis method, an experiment as shown in FIG. 6 was done. Two thickness gauges 11 of a same thickness l were interposed between an acrylic plate 9 of 5 mm in thickness and a polystyrol block 10 of 50 mm in thickness, and a layer 12 of a machine oil was formed in the space defined by these elements, thereby preparing an oil layer model.

A probe 13 of a 5 MHz split type was used and it was fixed to the acrylic plate 9 using an instantaneous adhesive.

Figure 7:
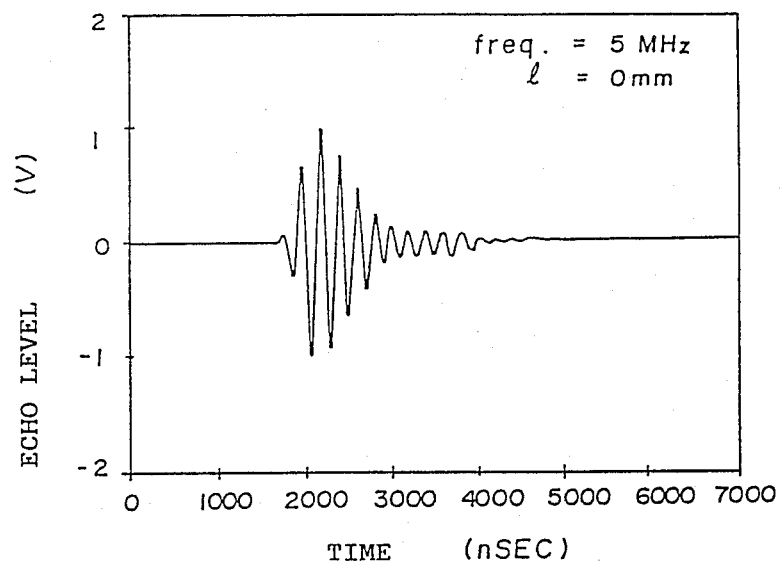
FIG. 7 is a drawing showing the reflection waveform from the bottom face of the acrylic plate in the experimental apparatus in FIG. 6.
Figure 8:
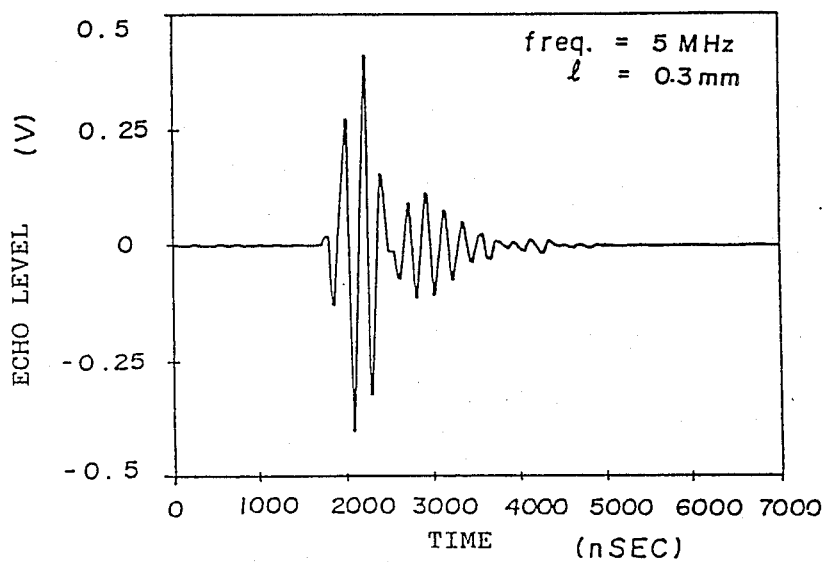
FIG. 8 is a drawing showing the reflection waveform which is the same as in FIG. 7 provided that the clearance (oil layer thickness) is 0.3 mm.

FIG. 7 shows the reflection waveform (fundamental waveform) from the bottom of the acrylic plate 9, and FIG. 8 shows the reflection waveform when l=0.3 mm. It is seen from these Figures that the mutual interference of the multiple-reflection waves in the oil layer causes the waveform to be deformed and the entire amplitude to be changed.

The reflection waves were sampled at intervals of 10 nsec with the thickness l of the thickness gauge 11 changed within a range of 0.1 to 1.0 mm and with the thickness of the oil layer changed, and an FFT cepstrum analysis was done using the algorithm shown in FIG. 3.

Figure 9:
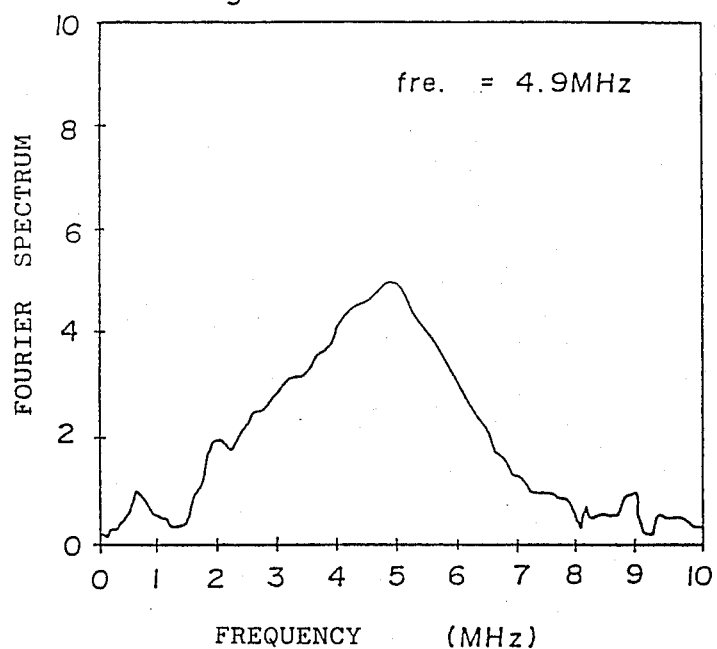
FIG. 9 is a drawing showing the result of a frequency analysis in the experimental apparatus shown in FIG. 6.
Figure 10:
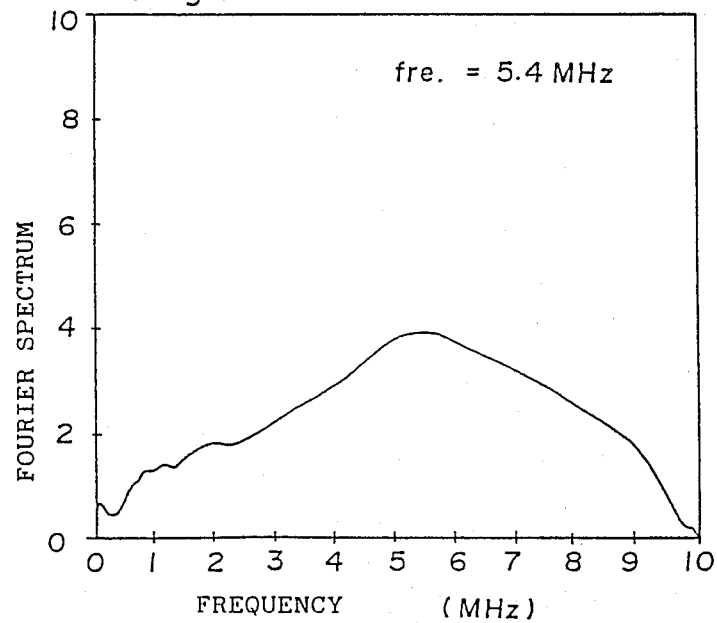
FIG. 10 is a drawing showing the result of a frequency analysis having been done using a different probe.

The results of frequency analysis of the 5-MHz split type probe used in the verification test and the 5-MHz split type probe used in the animal test which will be described later are shown in FIGS. 9 and 10. As seen from these Figures, the center frequencies of these probe are 4.9 MHz and 5.4 MHz, respectively and the frequency bands are limited to the ranges of about 2 to 7 MHz and 1 to 9 MHz, respectively.

On the assumption that the upper limit of the frequency band of a waveform is W (MHz), the minimum necessary sampling time $\Delta t$ (sec) for sampling a waveform signal can be obtained from the following equation and based on the sampling theorem:

$$\Delta t = \frac{1}{2W} \quad (5)$$

Since $\Delta t = 7.1 \times 10^{-8}$ (sec), the sampling time of $1.0 \times 10^{-8}$ (sec) used in this test can be said to be sufficient.

Figure 11:
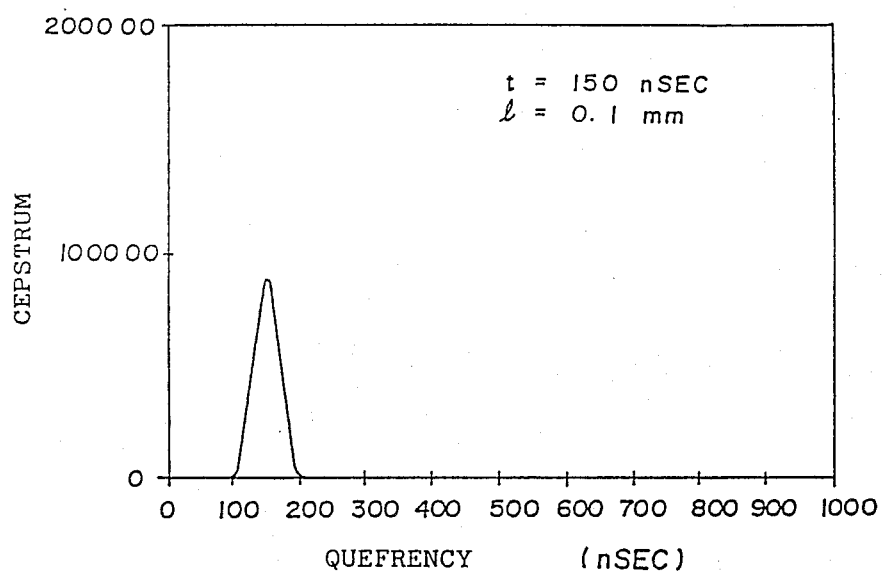
FIG. 11 is a drawing showing the time of a delay due to the oil layer when the clearance is 0.1 mm in the experimental apparatus in FIG. 6.
Figure 12:
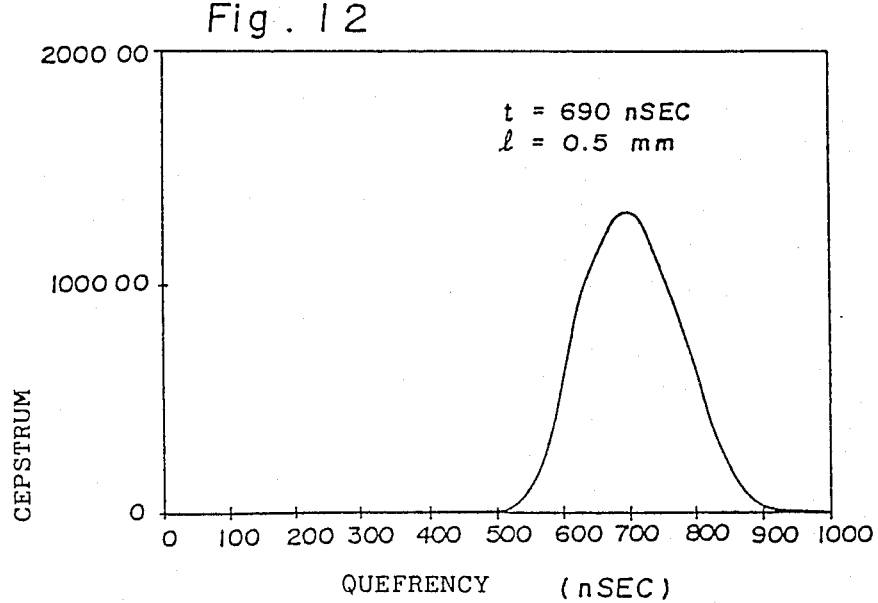
FIG. 12 is a similar drawing to that in FIG. 11, showing the time of a delay due to the oil layer when the clearance is 0.5 mm in the experimental apparatus.

FIG. 11 shows the result of the FFT cepstrum analysis of the reflection waveform when l=0.1 mm, and FIG. 12 shows the result of the FFT cepstrum analysis when l=0.5 mm.

These results were obtained using as time window the hamming window shown in the equation (6), and as cepstrum window the hanning digital window shown in the equation (8). The hanning window serves to weight the result of the cepstrum analysis and the hanning digital window serves to smooth the result of the cepstrum analysis.

$$W_{ham}(n) = 0.54 - 0.46 \cos(2n\pi/(N-1))\ldots \quad (6)$$

$$W_{han}(n) = 0.5 - 0.5 \cos(2n\pi/(N-1))\ldots \quad (7)$$

$$C'(n) = 0.25C(n-1) + 0.5C(n) + 0.25C(n+1)\ldots \quad (8)$$

As seen from FIGS. 11 and 12, the quefrency values at the peaks of the cepstrums are 150 nsec and 690 nsec, respectively. These quefrency values correspond to the delay time $\tau i$ in the equation (1).

The quefrency value at the peak of the cepstrum in FIGS. 11 and 12, that is, the time $\tau i$ of the delay due to the oil layer, correspond to the difference in time (time for reciprocation of the ultrasound in the oil layer) between the elements of the interference reflection wave. Therefore, the multiplication of this value by the acoustic velocity in the oil layer is the beam path. Hence, the thickness of the oil layer can be calculated by dividing the beam path by 2.

Figure 13:
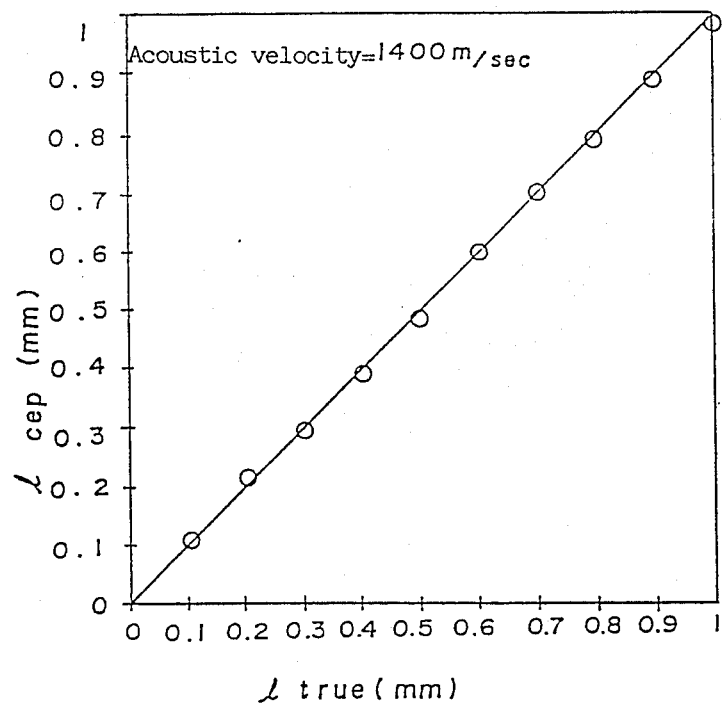
FIG. 13 is a drawing showing the comparison between the oil layer thickness determined by the cepstrum analysis and the real value.

The comparison between the oil layer thickness lcep calculated from the delay time determined by the cepstrum analysis and the thickness of the thickness gauge as true oil layer thickness ltrue is shown in FIG. 13. The calculation was done taking the acoustic velocity of the machine oil as 1,400 m/sec. As seen in FIG. 13, the oil layer thickness values are very similar to each other with the difference of about $+/-10$ $\mu$m. Thus, the cepstrum analysis is effectively usable in analysis of the delay time of each of more than one waves which interfere with each other. So when the acoustic velocity is already known, the use of this cepstrum analysis makes it possible to measure the thickness of a thin layer which could not otherwise be measured.

Next, the following experiments were done with the dog in order to review whether or not the verification done with the aforementioned apparatus is applicable to a living body or patient.

The experiments were done with a filial grown-up dog weighing about 10 kg. First, 5 to 6 ml of 2% (weight per volume) hydrochloric acid morphine was injected into th muscle of the dog for the basal anesthesia. Thereafter, 100 to 150 mg of thiamylal sodium was administered to the dog by intravenous injection for insufflation anesthesia, and the dog was placed in prone position under an endotracheal tube with the head immobilized on the Tohdai-Nohken stereotaxic table for use with dogs (this table was developed by the Tohdai-Nohken=the Brain Research Institute of Tokyo University). Thereafter, 10 to 15 mg of thiamylal sodium was additionally administered to the dog at every about 60 minutes for maintenance anesthesia as necessary and thus the experiment was done while the dog was keeping the spontaneous natural breathing.

Figure 14:
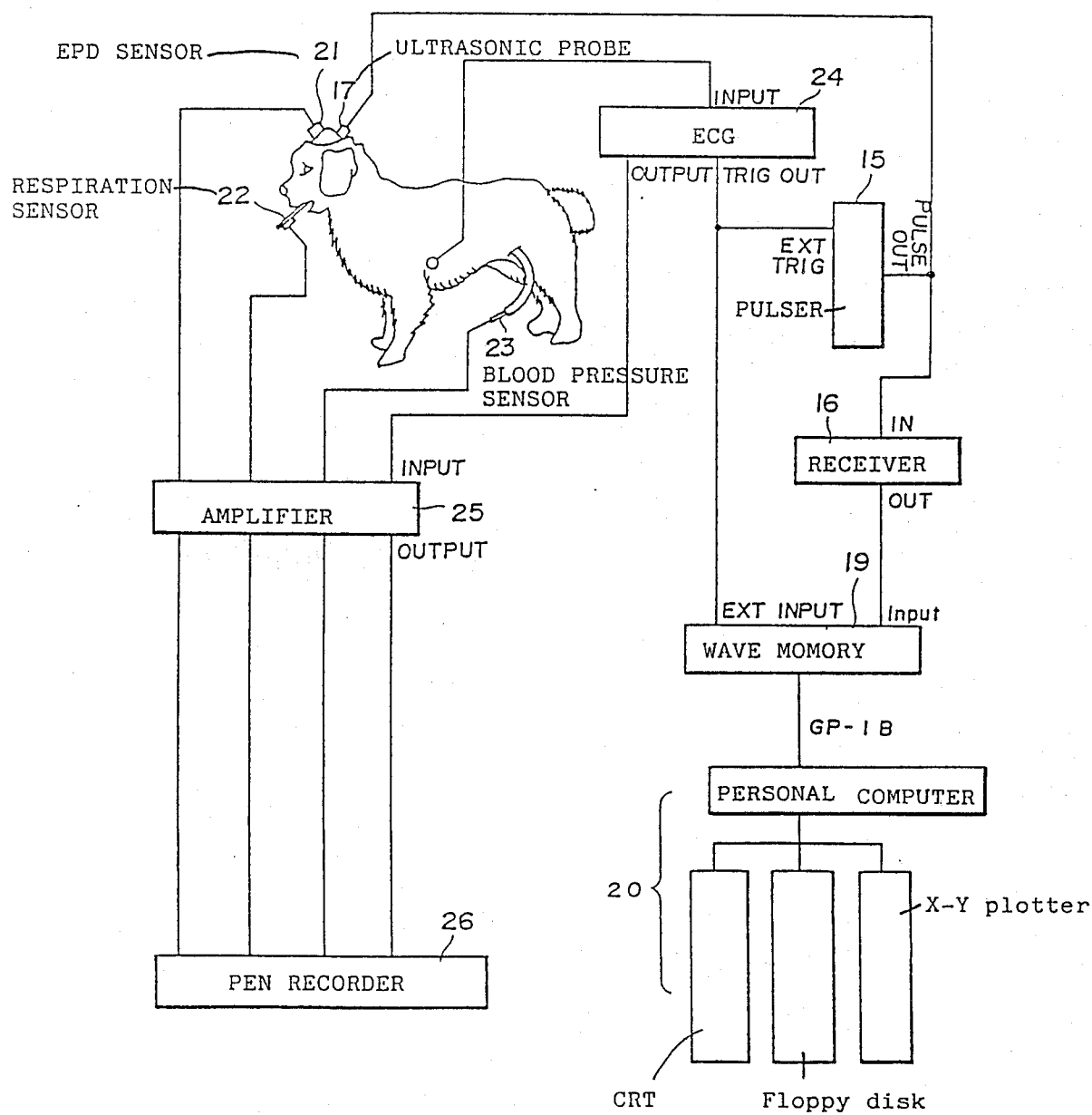
FIG. 14 is a block diagram of the experimental apparatus used in a test on a dog.

The block diagram of the experimental system is shown in FIG. 14. In the Figure, the reference numeral 15 indicates pulser, and 16 a receiver which receives and sends an electric signal with respect to an ultrasonic probe 17 which transduces an electric signal sent from the pulser 15 into an ultrasound or ultrasonic wave and also transduces a received ultrasonic wave into an electric signal. The reference numeral 19 indicates a wave memory to provide a high speed A/D conversion of a received waveform (analog signal), and 20 generally indicates a system composed of a personal computer, CRT, floppy disk unit and an X-Y plotter, that is, a so-called data processing system to process, analyzes, monitors and records a received waveform having been digitized by the wave memory 19. The reference numeral 21 indicates an EDP sensor placed outside the dura mater and which transduces an intracranial pressure into an electric signal, 22 a respiration sensor which pick up the respiration as a change of temperature and transduces a change of breathing into an electric signal, 23 a blood pressure sensor which monitors the systemic blood pressure and transduces a blood pressure into an electric signal, 24 an electrocardiograph (ECG) which produces an ECG waveform and generates a trigger signal as delayed an arbitrary time from the R-wave of the electrocardiogram (ECG), 25 an amplifier which amplifies signals sent from the EDP sensor 21, respiration sensor 22, blood pressure sensor 23 and ECG 24, and 26 a pen recorder which continuously records the ECG waveform, respiration waveform, systemic blood pressure waveform and EDP sensor-generated intracranial pressure waveform all amplified by the amplifier 25.

In the experiments, the intracranial pressure detected by the EDP sensor, systemic blood pressure, ECG and respiration were monitored besides the intracranial pressure measured with the ultrasonic technique. For measurement of the intracranial pressure by the EDP sensor 21, the EDP sensor 21 was attached on the right side of the dog's head and the extradural pressure was measured. The systemic blood pressure was measured with a catheter of 2 mm in inside diameter and about 400 mm in length inserted from the femoral artery and self-retained in the thoracic aorta and by a catheter-tip type pressure gauge. The ECG was measured by the ECG 24 having the electrodes thereof attached on the four extremities, respectively, of the dog. The respiration was measured using a thermistor probe attached to the tip of the endotracheal tube.

The experiments using the ultrasonic technique were conducted as follows:

As shown in FIG. 14, the entire experimental system was triggered with an ECG trigger with the trigger pulse from the ECG 24 so adjusted to be generated as delayed 80 msec from the peak of the R-wave in the ECG (electrocardiogram).

Figure 15:
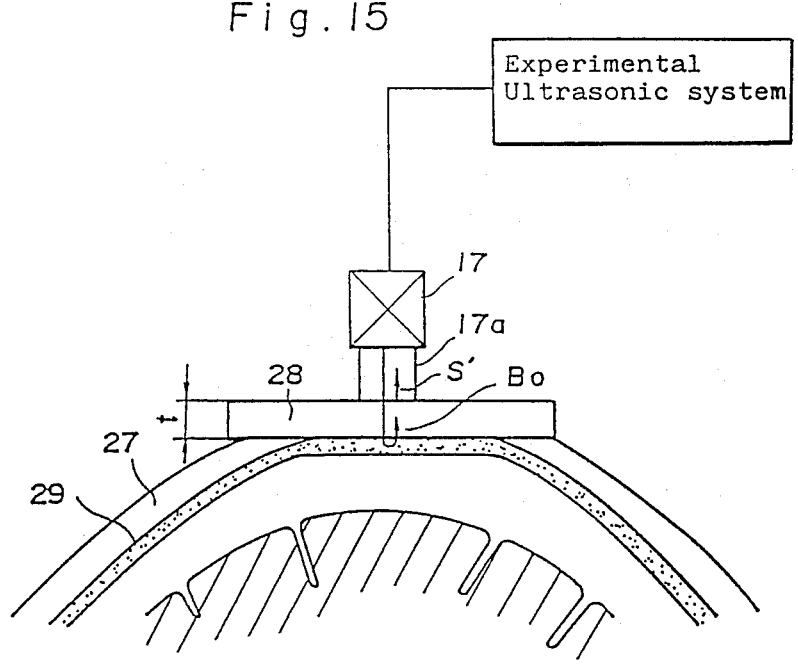
FIG. 15 is an explanatory drawing on the contact on the dog head of the probe in FIG. 14.

The experiment was done on two models with a saline injected into the cisterna magna to cause a sthenia of the intracranial pressure within a range of 0 to 650 mmH$_2$O. One of the models is an acrylic plate model in which an acrylic plate 28 of 5 mm in thickness (t) was introduced through an opening formed in the skull 27 and fixed as closely attached to the dura mater 29 as shown in FIG. 15 and a 5 MHz delayed-type probe was used for measurement. In another model, a 5 MHz split-type probe was fixed on the skull 27 and the measurement was done from on the skull 27. The reflection waves received by the receiver 16 were supplied to the wave memory 19, sampled at intervals of 10 msec and transferred via a GP-IB interface to the personal computer in which a data including digital values of the interference waves including the multiple reflections within the dura mater are extracted for analysis.

Figure 16A:
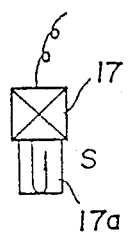
FIG. 16 is a drawing showing the reflection echo (S echo) from the surface of the delaying member in the probe shown in FIG. 15.
Figure 16:
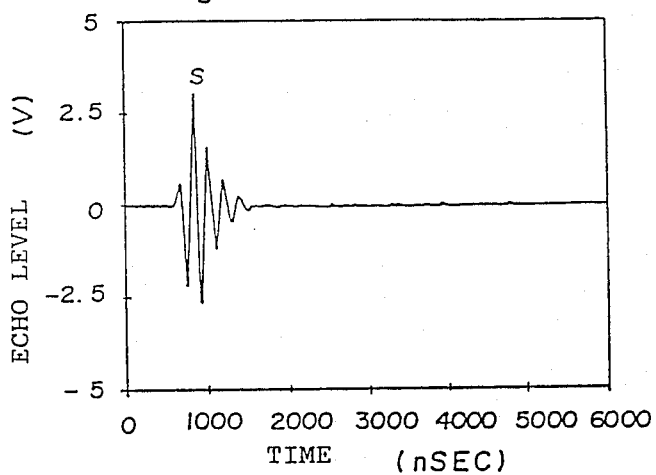
Figure 17A:
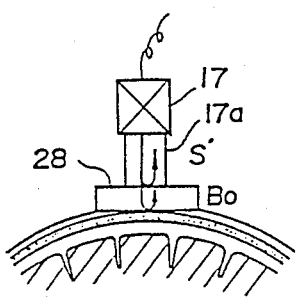
FIG. 17 is a drawing showing the reflection echoes (S' echo and Bo echo) from the boundaries shown in FIG. 15.
Figure 17:
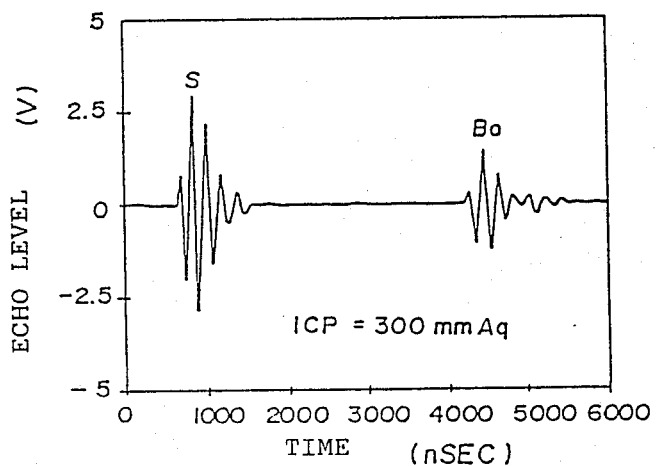

FIGS. 16 and 17 show, respectively, a received waveform of the surface reflection (S echo) from a delaying material 17a, and a received wave of the surface reflection (S echo) when the intracranial pressure (ICP) is 300 mmH$_2$O, which are the fundamental waveforms in the experiment by the acrylic plate model shown in FIG. 15. As seen from the Figures, the reflection wave (S' echo from the boundary between the surface of the delaying material 17a and the acrylic plate 28 is completely separate from the interference reflection wave (Bo echo) from near the boundary between the acrylic plate 28 and the dura mater 29 and there is little difference in waveform shape between the S and S' echoes. On the other hand, it will be seen that the Bo echo causes an interference due to the multiple reflections inside the dura mater 29 and is different in waveform shape from the S echo.

Figure 18:
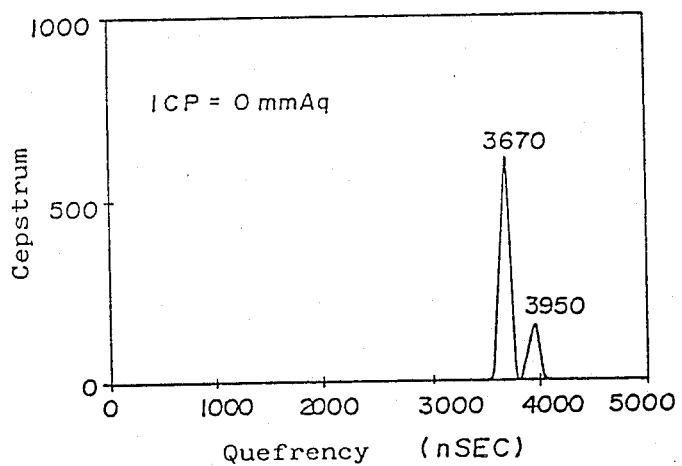
FIG. 18 is a drawing showing the result of a cepstrum analysis of the interference reflection echoes shown in FIGS. 16 and 17 when the intracranial pressure is 0 mmH$_2$O.
Figure 19:
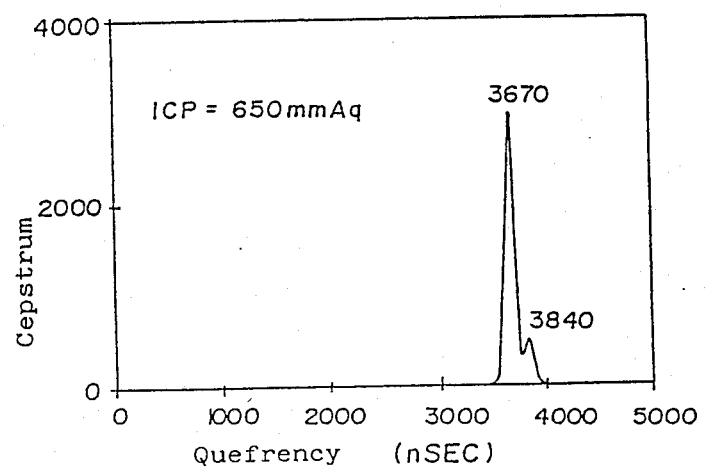
FIG. 19 is a similar drawing to that in FIG. 18 provided that the intracranial pressure is 650 mmH$_2$O.

FIGS. 18 and 19 show, respectively, the example results of the cepstrum analysis made on the assumption that the S echo is the fundamental waveform b(t) and the S' and Bo echoes are the reflection waveform x(t). FIG. 18 shows the result of the cepstrum analysis when the intracranial pressure is 0 mmH$_2$O while FIG. 19 shows the result when the intracranial pressure is 650 mmH$_2$O. The numerical values above the peaks indicate the quefrency values at the peak positions.

The quefrency value at the first peak is constant irrespectively of the intracranial pressure and indicates the time for reciprocal propagation of the ultrasonic wave between the surface of the delaying material 17a and the boundary between the acrylic plate 28 and dura mater 29. The difference in quefrency value between the second and first peaks is the time of a delay due to the dura mater 29 and equal to the time for reciprocal propagation of the ultrasonic wave within the dura mater 29.

The thickness calculation of the acrylic plate 28 from each quefrency value on the assumption that the acoustic velocity of the acrylic plate 28 is 2,730 m/sec while that of the dura mater 29 is 1,620 m/sec results in 5.01 mm which closely corresponds to the real thickness of 5 mm. The thickness of the dura mater 29 is calculated to be 227 $\mu$m (when the intracranial pressure is 0 mmH$_2$O and 138 $\mu$m (when the intracranial pressure is 650 mmH$_2$O), which reveals that the thickness of the dura mater is smaller as the intracranial pressure increases.

Figure 20:
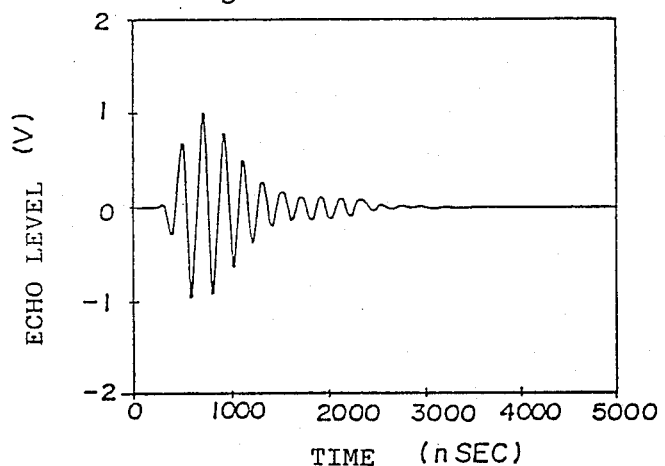
FIG. 20 is a drawing showing the S echo when the probe is placed in direct contact with the skull, not with an acrylic plate placed between the probe and skull.
Figure 21:
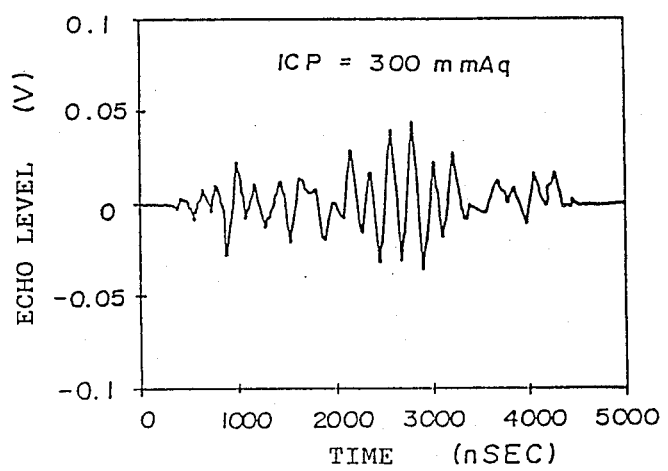
FIG. 21 is a similar drawing to that in FIG. 20, showing the S' echo and Bo echo.

Next, the results of the experiments by the measurement by an ultrasonic probe positioned on the skull 27 will be described below:

The fundamental wave b(t) is shown in FIG. 20, and the reflection waveform x(t) is shown in FIG. 21. The probe used was a 5 MHz split-type one.

The skull 27 is a three-layer structure consisting of an outer table, diploe and inner table and so the ultrasonic wave is reflected at each boundary. Since the dog's skull is of a thin structure, the reflection waves from the boundaries are not separable. Therefore, each reflection wave and the multiple reflections inside the dura mater interfere with each other so that the reflection waveform takes a complicate shape as shown in FIG. 21.

Figure 22:
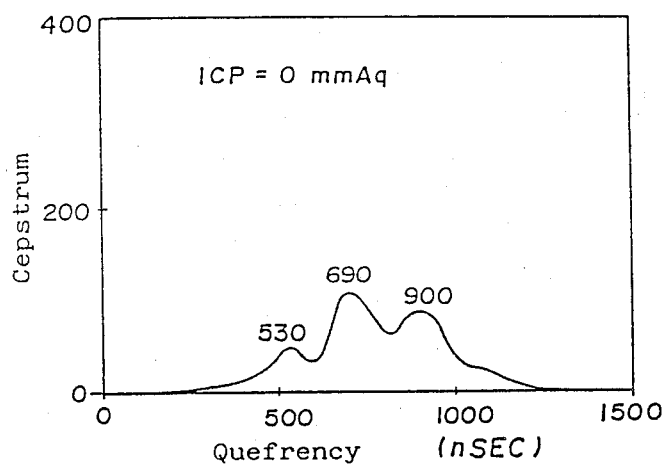
FIG. 22 is a drawing showing the result of a cepstrum analysis of the interference reflection echo as in FIGS. 20 and 21 when the intracranial pressure is 0 mmH$_2$O.
Figure 23:
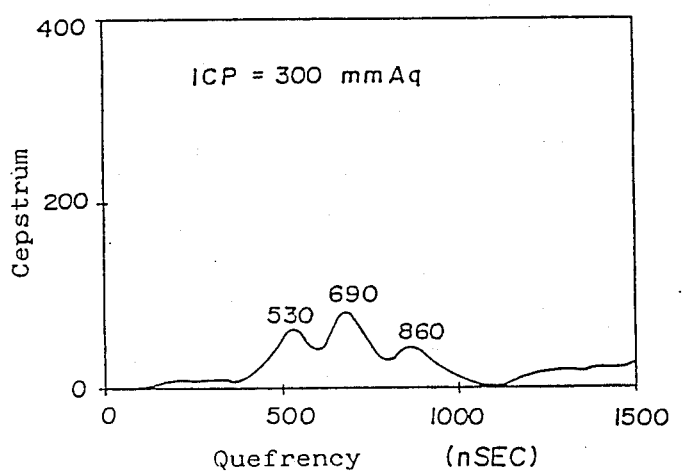
FIG. 23 is a similar drawing to that in FIG. 22 provided that the intracranial pressure is 300 mmH$_2$O.

FIGS. 22 and 23 show, respectively, the example results of the FFT cepstrum analysis of the reflection waveform in the experiments by the measurement with the probe placed on the skull 27. FIG. 22 shows the result when the intracranial pressure (ICP) is 0 mmH$_2$O while FIG. 23 shows the result when the intracranial pressure is 300 mmH$_2$O. In Figures, the numerical value above each peak indicates a quefrency value at each peak position.

The first and second peaks indicate, respectively, the quefrency values constant irrespectively of the intracranial pressure and also the lengths of time for reciprocal propagation between the diploe and the dura mater 29 of the skull 27 and between the inner table and the dura mater 29. The difference in quefrency value between the third and second peaks corresponds to the time for reciprocal propagation of the ultrasonic wave within the dura mater 29.

The thickness of the dura mater 29 calculated from the acoustic velocity thereof is 170 μm when the intracranial pressure is 0 mmH$_2$O while is 138 μm when the intracranial pressure is 300 mmH$_2$O, from which it is seen that as in the result of the experiments on the acrylic plate model, the dura meter thickness is smaller as the intracranial pressure increases.

Since the thickness of the dura mater 29 varies more or less from one living body or patient to another, the relation between the intracranial pressure and the dura mater thickness varies from one living body to another. In this respect, the quotient of the division of the change of the dura mater as the result of the increase of the intracranial pressure by the dura mater thickness before the intracranial pressure was increased (the dura mater thickness when the intracranial pressure is normal) was taken as the thickness strain of the dura mater, and the relation of this dura mater thickness strain with the intracranial pressure was determined.

Assuming that the dura mater thickness when the intracranial pressure shows the fundamental value p is D(p) while the dura mater thickness before the intracranial pressure is increased is Do, the thickness strain ϵ(p) is expressed as follows:

$$\epsilon(p) = \frac{D(p) - Do}{Do} \quad (9)$$

Figure 24:
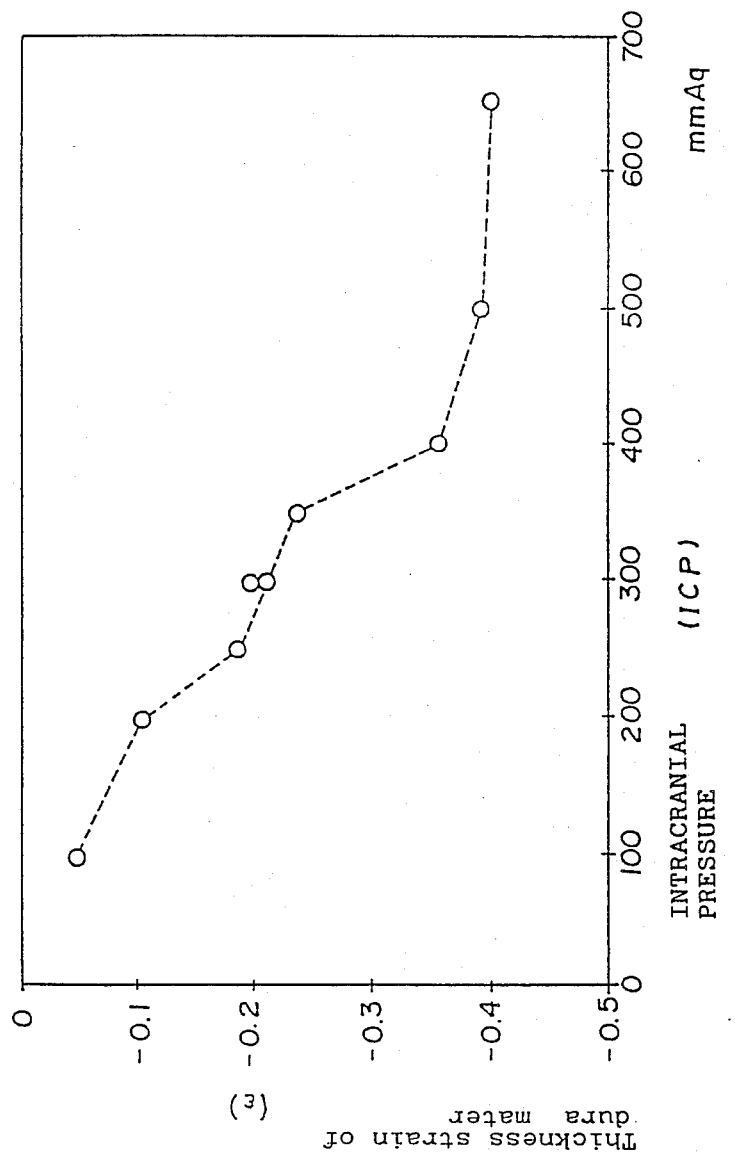
FIG. 24 is a drawing showing the relation between the intracranial pressure and strain of the dura mater, determined by the experiment shown in FIG. 14.

FIG. 24 shows the relation between the dura mater thickness strain ϵ determined by the equation (9) and the intracranial pressure fundamental value (ICP), which was obtained from the results of cepstrum analysis of the measurements by the acrylic plate model and from one the skull when the intracranial pressure was increased. The reason why the value ϵ is negative is that the dura mater is compressed under the increased intracranial pressure, as seen from the equation (9).

As seen from FIG. 24, up to the intracranial pressure of about 500 mmH$_2$O, the thickness strain of the dura mater increases gradually as the intracranial pressure increases, but as the intracranial pressure increases further from that point, the thickness strain asymptotically gets near a certain value. This tendency well corresponds to the phenomenon found in the previously mentioned constriction experiment on the intradural veins, which also suggests that the intracranial pressure fundamental value can be known by measuring the thickness strain ϵ of the dura mater but there exists a critical value beyond which no measurement can be done.

To determine the thickness strain ϵ of the dura mater, it is necessary to know a dura mater thickness which is the standard value when the intracranial pressure is normal. However, since the thickness of the dura mater differs from one living body or patient, one age and one measuring point from another, it is necessary to periodically measure the normal thickness of the dura mater peculiar to each living body similarly to his blood pressure, weight, etc. Thereby, it is possible to obtain a highly reliable diagnostic information, that is, time transition of the intracranial pressure and latest information, which can be simultaneously valuable clinical and therapeutic information and lesion-preventive information.

In the foregoing, the measurements of intracranial pressure of a grown-up dog by the apparatus according to the present invention have been described. When such measurement is applied to a human body, it is necessary to taken in consideration the differences in shape and size of his cranium and encephalomeninges from the dog's. Concerning, for example, the skull, both the dog's cranial volume and curvature are small and the irregularities on the inner wall are large, but the cranial volume and curvature of the human being's skull are both large and the irregularities on the inner wall are extremely small. Thus, the probe can be easily attached on the human being's skull and the ultrasound wave can be smoothly transmitted and reflected. Also, the dog's dura mater thickness is about 0.2 mm while the human being's dura mater thickness is about 1.0 mm, which means that the change of human being's dura mater thickness due to the change of the intracranial pressure will be about 5 times larger than that of the dog under the assumption that the change occurs at a same rate, which suggests that the intracranial pressure of human being can be measured with a correspondingly higher accuracy, for the intracranial pressure is measured with the apparatus according to the invention utilizing the correlation between the change of dura matter thickness and the intracranial pressure.

By the way, any measuring apparatus intended for use with the human being must be quite safe without any danger. For the apparatus according to the present invention, it must be proved that the ultrasound transmitted into the cranial when measuring the intracranial pressure does not adversely affect the cranium itself and the human body. For this issue, the following report has been publicized. It reads as follows. Namely, concerning the influence of the ultrasound on the chromosome, it was provided that the irradiation of an ultrasound of 500 mW/cm$^2$ in mean output and 50 W/cm$^2$ in peak output to the human peripheral lymphatic corpuscles in the premitotic period for 60 minutes shows no influence on the lymphatic corpuscles. Also, it was proved that an ultrasound of about 600 mW/cm$^2$ at maximum in mean output has no danger to the flowing red blood corpuscles, growth of cultured cells, and embryo or fetus. The mean output of the ultrasound used in the embodiment of the present invention is about 0.1 mW/cm$^2$, and so has no influence on the human body. Therefore, it can be said that the apparatus according to the present invention has no problem as to the safety to the human body.

As having been described in the foregoing, the apparatus according to the present invention transmits an ultrasound or ultrasonic wave from a probe into a living body or patient from outside the cranium, makes a frequency analysis of the echo of interference wave derived from the multiple reflections inside the cranium and calculates the time difference between the element waves of the interference wave, by an arithmetic unit, to measure the thickness of the dura mater, thereby measuring the intracranial pressure and its change from the correlation between the intracranial pressure and the dura mater thickness. Thus, the apparatus according to the present invention can measure the intracranial pressure easily, safely, noninvasively, highly reliably and without any adverse affect on the brain inside. Furthermore, by periodically effecting such measurement by the apparatus according to the present invention, a highly reliable diagnostic information on the pathology and a lesion-preventive information can be provided.

What is claimed is:

1. In an apparatus for measuring intracranial pressure, including an electrocardiograph for detecting a heartbeat of a living body having a cranium, a pulser means for generating a voltage pulse using the heartbeat detected by the electrocardiograph as a trigger, an ultrasonic probe means for receiving the voltage pulse generated by the pulser means and for transmitting an ultrasonic pulse into the cranium of the body from the outside thereof and for receiving an echo of an incident wave therefrom, a receiver means for amplifying the received echo and for providing an output corresponding thereto, a processor means for processing the output of the receiver means comprising:

an A/D converter means for digitizing discrete values of a waveform of the echo received by the probe means and for providing an output corresponding thereto; and an arithmetic means for extracting from the output of the A/D converter means a range including a reflection wave from dura mater of a certain thickness contained within the cranium, and for determining a time difference between element waves from a quefrency value obtained through frequency analysis of the extracted range by an arithmetic algorithm of a cepstrum method so as to calculate the thickness of the dura mater, and for comparing the calculated dura mater thickness with a previously measured reference value so as to calculate a dura mater distortion factor having a correlation with an intracranial pressure within the cranium.

2. In an apparatus for measuring intracranial pressure, including an electrocardiograph for detecting a heartbeat of a living body having a cranium, a pulser means for generating a voltage pulse using the heartbeat detected by the electrocardiograph as a trigger, an ultrasonic probe means for receiving the voltage pulse generated by the pulser and for transmitting an ultrasonic pulse into the cranium of the body from the outside thereof and for receiving an echo of an incident wave therefrom, a receiver means for amplifying the received echo and for providing an output corresponding thereto, a processor means for processing the output from the receiver means comprising:

a gate circuit means for gating the echo received by the probe means to a range including reflection waves from dura mater of a certain thickness contained within the cranium and for outputting a waveform corresponding thereto;

an A/D converter for digitizing discrete values of the output waveform from the gate circuit means and for providing an output corresponding thereto; and an arithmetic means for determining a time difference between element waves from a quefrency value obtained through frequency analysis of the output of the A/D converter by the arithmetic algorithm of a cepstrum method, so as to calculate the thickness of the dura mater and for comparing the calculated dura mater thickness with a previously measured reference value so as to calculate a dura mater distortion factor having a correlation with an intracranial pressure within the cranium.

* * * * *